US00PP09573P

United States Patent [19]

Noack

[11] Patent Number: Plant 9,573

[45] Date of Patent: Jun. 11, 1996

[54] GROUND COVER ROSE PLANT NAMED 'FLOWER CARPET WHITE'

[76] Inventor: Werner Noack, Im Fenne 60, 33334 Gütersloh, Germany

[21] Appl. No.: 508,048

[22] Filed: Jul. 27, 1995

[51] Int. Cl.[6] ..... A01H 5/00

[52] U.S. Cl. ..... Plt./1

[58] Field of Search ..... Plt./1, 23, 8.1

*Primary Examiner*—Howard J. Locker

*Attorney, Agent, or Firm*—Burns, Doane, Swecker & Mathis

[57] ABSTRACT

A new and distinct variety of ground cover rose plant is provided which forms continuously throughout the season attractive long-lasting pure white blossoms. The new variety exhibits a compact and spreading growth habit that renders it suitable for growing as an ornamental ground cover in the landscape. The foliage is dark green and glossy and contrasts well with the pure white blossoms. Reproductive organs and pollen provide a generally yellow coloration at the center of each fully open blossom. The pure white blossom coloration is well retained upon the aging of the blossoms, and petals drop off cleanly as the blossoms mature. The new variety also propagates well from cuttings, by the budding of an eye, and by grafting, and exhibits an excellent resistance to blackspot, mildew, and rust.

2 Drawing Sheets

SUMMARY OF THE INVENTION

The new variety of ground cover rose plant of the present invention was created by artificial pollination wherein two parents were crossed which previously had been studied in the hope that they would contribute the desired charcteristics. The female parent (i.e., the seed parent) was the 'Flower Carpet' variety (U.S. Plant Pat. No. 7,282) which sometimes is known as the 'Noatraum' variety. The 'Flower Carpet' variety is marketed under the Heidetraum trademark in Germany, and possesses deep pink blossoms. The male parent (i.e., the pollen parent) 'Margaret Merril' variety (non-patented in the United States) which is a Floribunda variety possessing white blossoms. The 'Margaret Merril' variety sometimes is known as the 'Harkuly' variety. The parentage of the new variety can be summarized as follows:

*'Flower Carpet'×'Margaret Merril'.*

The seeds resulting from the above pollination were sown and small plants were obtained which physically and biologically differ from each other. Selective study resulted in the identification of a single plant of the new variety.

It is found that the new ground cover rose plant possesses the following combination of characteristics:

(a) forms attractive pure white, long-lasting blossoms substantially throughout the season that well retain their original coloration upon aging,
(b) exhibits a compact and spreading growth habit,
(c) forms attractive dark green and glossy foliage that contrasts well with the pure white blossoms,
(d) exhibits excellent disease resistance with respect to blackspot, mildew, and rust, and
(e) is particularly suited for growing as attractive ornamentation in the landscape.

Reproductive organs and pollen provide a generally yellow coloration at the center of each fully open blossom.

The new variety meets the needs of the horticultural industry and can be grown to advantage as attractive ornamentation in parks, gardens, public areas, and residential landscapes.

The new variety of the present invention has been found to readily undergo asexual reproduction in Germany by the use of cuttings, by the budding of an eye, and by grafting.

Such asexual reproduction as performed in Germany has shown that the characteristics of the new variety are homogeneous and stable and are strictly transmissible from one generation to another.

The new variety has been named the 'Flower Carpet White' variety. The new variety also is known as the 'Noaschnee' variety in Europe and is being marketed under the Schneeflocke trademark in Europe.

BRIEF DESCRIPTION OF THE PHOTOGRAPHS

The accompanying photographs show as nearly true as it is reasonably possible to make the same, in color illustrations of this character, typical specimens of the new variety while growing in the landscape. The illustrated rose plants were three years of age and were observed during July while growing outdoors on 'Pfänders' understock at Gütersloh, Germany.

FIG. 1 illustrates a profusion of blossoms and the foliage of the new variety wherein the buds and blossoms are visible in various stages of opening and the good petal drop character of the new variety is visible as the blossoms mature; and FIG. 2 illustrate buds, blossoms, and foliage of the new variety in greater detail that as illustrated in FIG. 1.

DETAILED DESCRIPTION

The chart used in the identification of the colors is that of The Royal Horticultural Society (R.H.S. Colour Chart) of London, England. Color terminology in common terms sometimes is included as an aid to the reader. The description is based on the observation of three year-old specimens of the new variety while growing outdoors on 'Pfänders' understock during June and July at Gütersloh, Germany.

Class: Ground Cover.

Parentage:

*Female.*—'Flower Carpet' (U.S. Plant Pat. No. 7,282).

*Male.*—'Margaret Merril' (non-patented in the United States).

Plant:

*Height.*—Approximately 50 cm. on average at the end of the growing season.

*Form.*—Compact and spreading, and creates an excellent ground cover.

Branches:

*Color.*—Young stems: light green, and with a smooth surface. Adult wood: medium green and with a smooth surface.

*Thorns.*—Size: medium, approximately 5 mm. in length on average, and slightly curved downward. Frequency: irrgular. Color: initially light brown changing to dark brown with maturity.

Leaves:

*Stipules.*—Light green in coloration.

Figure 1:
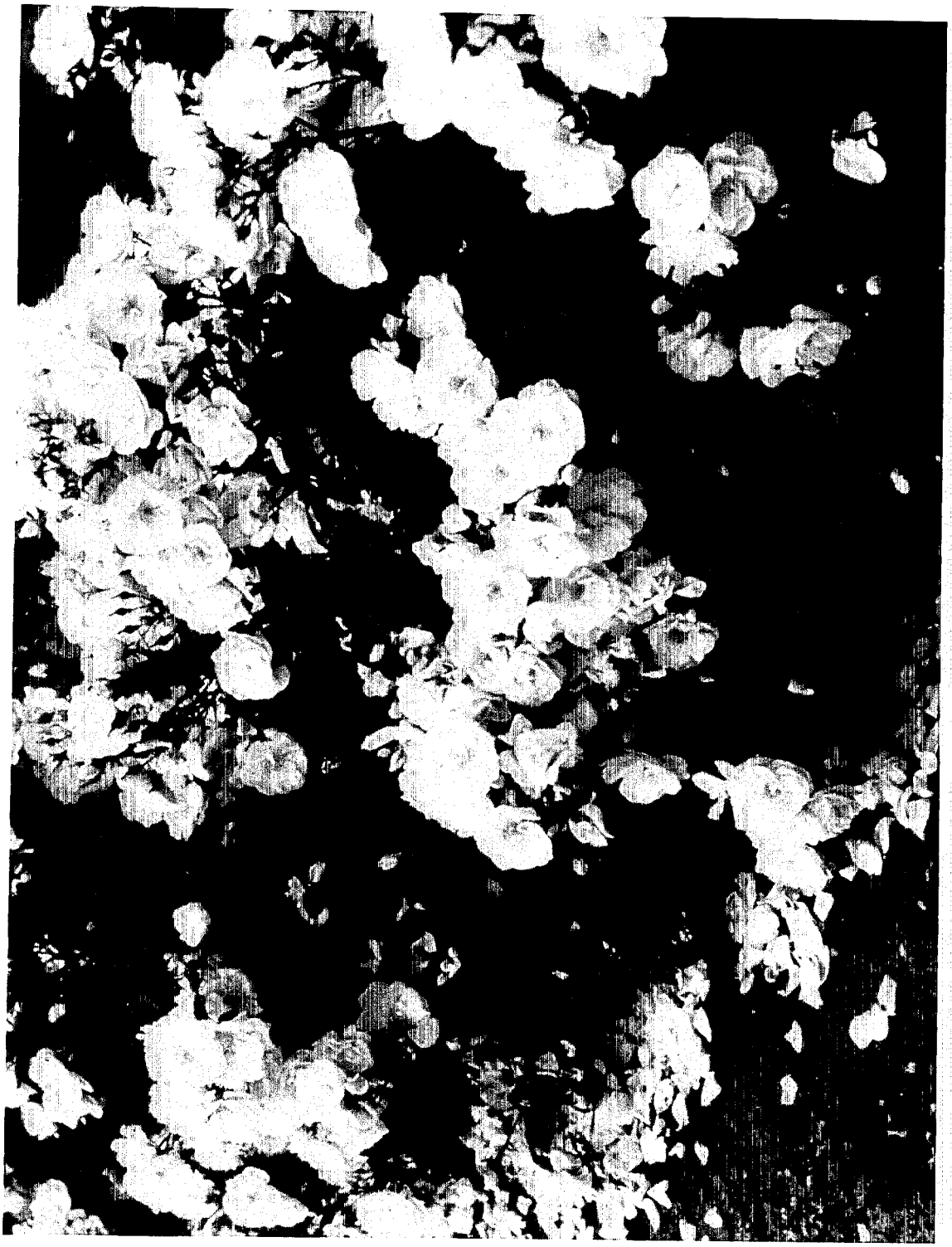
Figure 2:
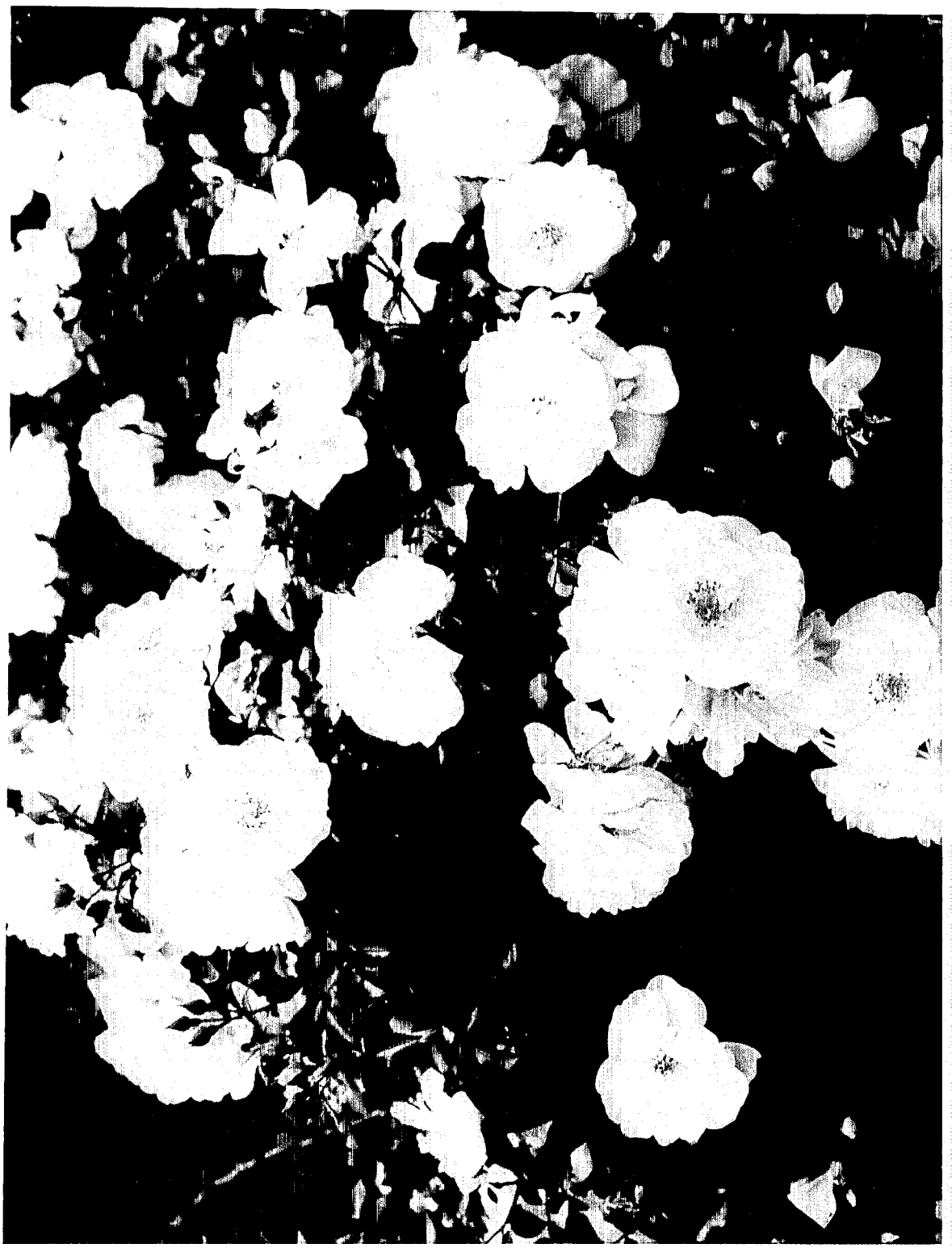

*Leaflets.*—Number: commonly 5 to 7. Quantity: very abundant. Size: medium. Serration: simple. Color (young foliage): Upper surface: bronze as illustrated in FIG. 2. Under surface: slightly lighter than upper surface. Color (adult foliage): Upper surface: dark green and glossy as illustrated in FIG. 2. Under surface: slightly lighter than upper surface and matte. General appearance: dense, dark green, and glossy. Texture: leathery.

Inflorescence:

*Number of flowers.*—Numerous and commonly in clusters.

*Peduncle.*—Light green in coloration, short in length, relatively strong, and commonly crooked.

*Sepals.*—Commonly extend beyond the bud and are pointed.

*Buds.*—Shape: rounded as illustrated in FIG. 2. Length: approximately 3 cm. on average. Size: medium. Color when opening: Upper surface: White, White Group 155B. Under surface: White, White Group 155B.

*Flower.*—Form: initially cup-shaped with flattening upon maturity. Diameter: approximately 6 cm. on average. Color (when opening begins): Upper surface: White, White Group 155B. Under surface: White, White Group 155B. Color (when blooming): Upper surface: White, White Group 155B. Under surface: White, White Group 155B. Color (at end of opening): Upper surface: White, White Group 155B. Under surface: White, White Group 155B. Fragrance: slight. Lasting quality: long on plant. Petal form: outer petals tend to have wavy edges (as illustrated), the inner petals commonly have edges that are slightly bent. Petaloids: commonly none. Petal number: approximately 16 on average. Petal arrangement: generally arranged in a regular pattern with overlapping edges. Petal drop: good with a clean disengagement of the petals. Stamens: approximately 60 on average, and regularly arranged around the styles. Filaments: nearly transparent in appearance. Pistils: commonly only one. Stigmas: cream yellow in coloration. Styles: thin, bunched, and tend to be of substantially the same length. Hips: small and orange-yellow in coloration.

Development:

*Vegetation.*—Strong.

*Blooming.*—Abundant and substantially continuous throughout the season.

*Aptitude to bear fruits.*—Good.

*Winter hardiness.*—Good.

*Resistance to diseases.*—Excellent with respect to blackspot, mildew, and rust.

I claim:

1. A new and distinct variety of ground cover rose plant characterized by the following combination of characteristics:

(a) forms attractive pure white, long-lasting blossoms substantially throughout the season that well retain their original coloration upon aging, (b) exhibits a compact and spreading growth habit, (c) forms attractive dark green and glossy foliage that contrasts well with the pure white blossoms, (d) exhibits excellent disease resistance with respect to blackspot, mildew, and rust, and (e) is particularly suited for growing as attractive ornamentation in the landscape;

substantially as herein shown and described.

* * * * *

UNITED STATES PATENT AND TRADEMARK OFFICE

CERTIFICATE OF CORRECTION

PATENT NO. : PP09,573
APPLICATION NO. : 08/508048
DATED : June 11, 1996
INVENTOR(S) : Werner Noack It is certified that error appears in the above-identified patent and that said Letters Patent is hereby corrected as shown below:

On the Title Page

1. Title Page, Title (item 54): delete "FLOWER CARPET WHITE" and insert -- 'NOASCHNEE' --.

2. Column 1, lines 7 through 8: delete "Flower Carpet" and insert -- 'Noatraum' --.

3. Column 1, lines 8 through 9: delete "which sometimes is known as the 'Noatraum' variety.".

4. Column 1, line 9: delete "Flower Carpet" and insert -- 'Noatraum' --.

5. Column 1, line 18: delete "Flower Carpet" and insert -- 'Noatraum' --.

6. Column 2, lines 5 through 6: delete "Flower Carpet White" and insert -- 'Noaschnee' --.

7. Column 2, line 39: delete "Flower Carpet" and insert -- 'Noatraum' --.

Signed and Sealed this
Fifth Day of August, 2014

Michelle K. Lee

Michelle K. Lee
*Deputy Director of the United States Patent and Trademark Office*